United States Patent [19]
Bryant et al.

[11] Patent Number: 5,578,613
[45] Date of Patent: Nov. 26, 1996

[54] METHODS FOR INHIBITING WEIGHT GAIN OR INDUCING WEIGHT LOSS

[75] Inventors: Henry U. Bryant; Jeffrey A. Dodge, both of Indianapolis, Ind.

[73] Assignee: Eli Lilly and Company, Indianapolis, India.

[21] Appl. No.: 171,291

[22] Filed: Dec. 21, 1993

[51] Int. Cl.$^6$ .................................................. A61K 31/445
[52] U.S. Cl. .......................... 514/324; 514/317; 514/319; 514/320; 514/909
[58] Field of Search ................................... 514/317, 319, 514/324, 320, 909

[56] References Cited

U.S. PATENT DOCUMENTS

| | | | |
|---|---|---|---|
| 4,133,814 | 1/1979 | Jones et al. | 260/326.55 |
| 4,380,635 | 4/1983 | Peters | 546/202 |
| 4,418,068 | 11/1983 | Jones | 424/267 |
| 5,075,321 | 12/1991 | Schreiber | 514/317 |

FOREIGN PATENT DOCUMENTS

| | | |
|---|---|---|
| WO93/10113 | 5/1993 | WIPO . |
| WO93/1074 | 6/1993 | WIPO . |

OTHER PUBLICATIONS

Draper et al., "Effects of Raloxifene (LY139481 HC1) on Biochemical Markers of Bone and Lipid Metabolism i Healthy Postmenopausal Women", Hong Kong, Fourth Int'l Symp. on Osteoporosis, Mar. 29, 1993.

Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.

Bryant et al., "Raloxifene is a Tissue Specific Estrogen Agonist", Am Soc. Bone & Min. Res., Tampa, Sep. 18–22, 1993.

Frolick et al., "In Vivo and In Vitro Metabolism of Raloxifene", Am Soc. Bone & Min. Res., Tampa, Sep. 18–22, 1993.

Glasebrook et al., "Multiple Binding Sites for the Anti–estrogen Raloxifene", Am Soc. Bone & Min. Res., Tampa, Sep. 18–22, 1993.

Hock et al., "Combination of Raloxifene and Human Parathyoid Hormone 1–34; Increased Femur Bone Mass in Young Ovariectomized (OVX) Rats", Am Soc. Bone & Min. Res., Tampa, Sep. 18–22, 1993.

Sato et al., "DEXA Analysis of Raloxifene Effects on the Bones From Ovariectomized Rats", Am. Soc. for Bone and Min. Res., Tampa, Sep. 18–22, 1993.

Yang et al., "Raloxifene an Anti–Estrogen, Simulates the Effects of Estrogen in Inhibiting Bone Resorption Through Regulating TGFB–3 Expression in Bone;". Am Soc. for Bone and Min. Res., Tampa, Sep. 18–22, 1993.

Black et al., "Distinct, Structure–Related Profiles of Estrogenic and Anti–Estrogenic Activity in the Tamoxifen and LY117018 Series;" The Endocrine Society, Abstract 1982.

Black et al., "Uterine Bioassay of Tamoxifen, Trioxifene, and New Estrogen Antagonist (LY117018) in Rats and Mice," Life Sciences, 26:1980, 1453–1458.

Black et al., "Differential Interaction of Antiestrogens with Cytosol Estrogen Receptors," Molecular and Cellular Endocrinology, 22:1981, 95–103.

Black et al., "Evidence for Biological Action of the Antiestrogens LY117018 and Tamoxifen by Different Mechanisms," Endocrinology 109;1981, 987–989.

Black, L. J. "Biological Actions and Binding Properites of a New Estrogen Antagosist LY117018," In: Homone Antagonists, 129–82, 1982 (M. K. Agarwal ed.) Walter de Gruyter and Co., Berlin New York.

Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32:1983. 1031–1036.

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

(List continued on next page.)

*Primary Examiner*—Shailendra Kumar
*Attorney, Agent, or Firm*—James J. Sales

[57] ABSTRACT

A method of inhibiting weight gain or inducing or facilitating weight loss comprising administering to a human an effective amount of a compound having the formula

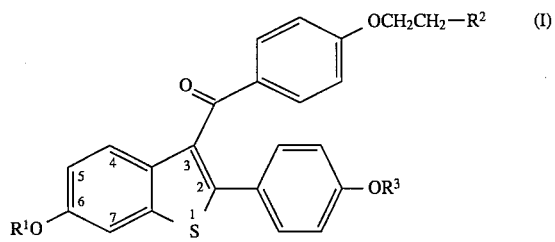

wherein $R^1$ and $R^3$ are independently hydrogen, —$CH_3$,

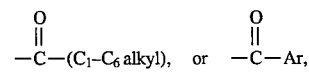

wherein Ar is optionally substituted phenyl;

$R^2$ is selected from the group consisting of pyrrolidino, hexamethyleneamino, and piperidino; or a pharmaceutically acceptable salt of solvate thereof.

5 Claims, No Drawings

OTHER PUBLICATIONS

Black et al., Synthesis and Antiestrogenic Activity of [3,4–Dihydro–2(4–methoxyphenyl)–1–napthalenyl] [4–[2–pyrrolidinyl) ethoxyl]–phenyl] methanone, methanesulfonic acid salt, Journal of Medicinal Chemistry 22;1979, 962–966.

Black et al., Antiestrogens 2. Structure Activity Studies in a Series of 3–Aroyl–2–arylbenzo[b]thiophene Derivatives Leading to [6–Hydroxy–2–(4–hydroxyphenyl)benzo[b]thien–3–yl] [4–[2–(1–piperidinyl)ethoxy]–phenyl]methanone Hydrochloride (LY156758), a Remarkably Effective Estrogen Antagonist with Only Minimal Intrinsic Estrogenicity, J. Med. Chem. 27(8), 1984, 1057–1066.

Neubauer B. L. et al., Endocrine and Antiprostatic Effects of Raloxifene (LY156758) in the Male Rat, The Prostate, vol. 23, No. 3, pp. 245–262, (1993).

Neubauer B. L. et al., Comparative Antitumor Effects of Hormonal Ablation, Estrogen Agonist, Estrogen Cytotoxic Derivatitve, and Antiestrogen in the PAIII Rat Prostatic Adenocarcinoma, Cancer Research, vol. 52, No. 17, pp. 4663–4671 (1992).

Gary J. M. et al., Estrogens and Antiestrogens: Actions and Interactions with Fluphenazine on Food Intake and Body Weight in Rats, American Journal of Physiology: Heart and Circulatory Physiology, vol. 33, No. 6, pp. R1214–R1218, Jun. 1993.

Wade G. N. et al., Tamoxifen mimics the effects of estradiol on food intake, body weight, and body composition in rats, American Journal of Physiology: Heart and Circulatory Physiology, vol. 33, No. 6, pp. R1219–R1223, Jun. 1993.

METHODS FOR INHIBITING WEIGHT GAIN OR INDUCING WEIGHT LOSS

BACKGROUND OF THE INVENTION

Western society places great emphasis on personal appearance and in particular one's weight. Diets and weight loss programs are extensively advertised and utilized by many people with varying degrees of success. There continues to be a search for new and effective means to facilitate weight loss.

Obesity is the most prevalent, chronic, medical condition in our society. Being overweight or obese is directly or indirectly associated with a vast number of diseases including hypertension, diabetes, cardiovascular disease, and gallstones, for example. Also, diminished self-image with consequent psychological maladjustments are linked to being overweight. As such, those who are overweight often experience more health problems and shortened life expectancies.

SUMMARY OF THE INVENTION

This invention provides methods for inhibiting weight gain or inducing weight loss comprising administering to a human an effective amount of a compound of formula I

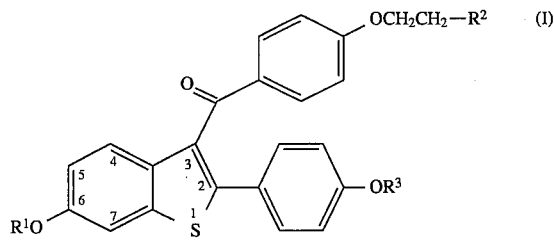

wherein $R^1$ and $R^3$ are independently hydrogen, —$CH_3$,

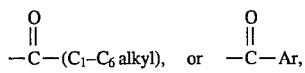

wherein Ar is optionally substituted phenyl;

$R^2$ is selected from the group consisting of pyrrolidino, hexamethyleneimino, and piperidino; and pharmaceutically acceptable salts and solvates thereof.

Also encompassed by the invention is a method of suppressing or inhibiting appetite which comprises administering to a human a compound of formula 1.

DETAILED DESCRIPTION OF THE INVENTION

The current invention concerns the discovery that a select group of 2-phenyl-3-aroylbenzothiophenes (benzothiophenes), those of formula I, are useful for inhibiting weight gain or inducing or facilitating weight loss, or inhibiting appetite. The methods of use provided by this invention are practiced by administering to a human a dose of a compound of formula I or a pharmaceutically acceptable salt or solvate thereof, effective to inhibit weight gain or induce weight loss, or inhibit appetite. The present method includes both medical therapeutic and/or prophylactic treatment, as appropriate.

The term "inhibit weight gain or induce weight loss" is defined to include its generally accepted meaning which includes administration to a human subject to weight gain, and holding in check or reducing a human's weight. The term "inhibit appetite" includes suppression or reduction of appetite. Also encompassed by the invention is the treatment of an obese human, inducement of weight loss in a human of relatively normal weight, and the maintenance of weight control.

Raloxifene, a preferred compound of this invention is the hydrochloride salt of a compound of formula 1, wherein $R^1$ and $R^3$ are hydrogen and $R^2$ is 1-piperidinyl, and is a nuclear regulatory molecule.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above. Optionally substituted phenyl includes phenyl or phenyl substituted once or twice with $C_1$–$C_6$ alkyl, $C_1$–$C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesutfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to inhibit weight gain or induce or facilitate weight loss, or inhibit appetite, according to this invention, will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need of treatment from once to about three times each day, or more often as needed.

It is usually preferred to administer a compound of formula I in the form of an acid addition salt, as is customary in the administration of pharmaceuticals bearing a basic group, such as the piperidino ring. It is also advantageous to administer such a compound by the oral route to an aging human (e.g. a post-menopausal female). For such purposes the following oral dosage forms are available.

Formulations

In the formulations which follow, "active ingredient" means a compound of formula I.

Formulation 1: Gelatin Capsules
Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

| Ingredient | Quantity (mg/capsule) |
| --- | --- |
| Formulation 2: Raloxifene capsule | |
| Raloxifene | 1 |
| Starch, NF | 112 |
| Starch flowable powder | 225.3 |
| Silicone fluid 350 centistokes | 1.7 |
| Formulation 3: Raloxifene capsule | |
| Raloxifene | 5 |
| Starch, NF | 108 |
| Starch flowable powder | 225.3 |
| Silicone fluid 350 centistokes | 1.7 |
| Formulation 4: Raloxifene capsule | |
| Raloxifene | 10 |
| Starch, NF | 103 |
| Starch flowable powder | 225.3 |
| Silicone fluid 350 centistokes | 1.7 |
| Formulation 5: Raloxifene capsule | |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
| --- | --- |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

Formulation 7: Tablets

| Ingredient | Quantity (mg/tablet) |
| --- | --- |
| Active ingredient | 0.1–1000 |
| Starch | 45 |
| Cellulose, microcrystalline | 35 |

-continued

| Formulation 7: Tablets | |
|---|---|
| Ingredient | Quantity (mg/tablet) |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

| Formulation 8: Suspensions | |
|---|---|
| Ingredient | Quantity (mg/5 ml) |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

TEST PROCEDURES

ASSAY 1

Between three and fifty rats (250–300 g) are individually housed in metal wire hanging cages. The animals are divided into one of three dosing groups: vehicle (20% cyclodextrin (CDX)); ethynyl estradiol ($EE_2$)(0.1 mg/kg) or a compound of formula 1 (10 mg/kg). The rats are given daily oral gavages for four consecutive days while having ad lib access to food and water. After the fourth daily dose, all food is removed from each of the animals' cages for a 24 hour period. After the food deprivation period, the animals are given a fifth oral gavage of the appropriate agent. Thirty minutes later, a pre-weighed allotment of lab chow is placed on the cage floor. The animals are allowed to feed for 2 hours after which any remaining food on the cage floor is collected along with large pieces which fall through the wire mesh floor. A second allotment is then given to each animal for an additional two hour period, and the residual food is collected as before. Food intake for each two hour period, and the four hour total, is calculated algebraically.

For a compound of formula 1 wherein $R^1$ and $R^3$ are hydrogen and $R^2$ is 1-pyrrolidino ("Compound A"), the following data is collected.

| | TIME (hr) | FOOD INTAKE (g) |
|---|---|---|
| Control Group (12 rats) | 2 | 4.83 ± 0.38 |
| | 4 | 7.17 ± 0.47 |
| $EE_2$ Group (6 rats) | 2 | 0.00 ± 0.00* |
| | 4 | 1.50 ± 0.00* |
| Compound A Group (6 rats) | 2 | 1.35 ± 0.87* |
| | 4 | 2.12 ± 1.00* |

* = $p \leq 0.05$ vs CDX control

ASSAY 2

Ovariectomized or sham surgeried rats are group housed in metal wire hanging cages Immediately following surgery, animals are given either control vehicle (1.5% carboxymethylcellulose), ethynyl estradiol (0.1 mg/kg) or a compound of formula 1 (0.01 to 10 mg/kg) by daily oral gavage. The animals have ad lib access to food and water. Body weight is determined after 35 days of dosing.

For raloxifene ("Ral") the following data is collected.

| GROUP | BODY WEIGHT CHANGE (g)[a] |
|---|---|
| Intact Control | 77.4 ± 3.1* |
| OVX Control | 120.3 ± 3.8 |
| OVX + $EE_2$ (0.1 mg/kg) | 18.0 ± 4.0* |
| OVX + Ral (0.01 mg/kg) | 108.6 ± 4.0 |
| OVX + Ral (0.1 mg/kg) | 70.5 ± 3.7* |
| OVX + Ral (1 mg/kg) | 62.2 ± 3.0* |
| OVX + Ral (10 mg/kg) | 53.7 ± 2.8* |

[a] = mean body weight ± SEM for for 28(intact control), 29(OVX control), 12 ($EE_2$), or 30 (each raloxifene dose) rats per group.
* = $p \leq 0.05$ vs OVX control by Scheffe range test.

Other feeding paradigms

Nocturnal (12 hr) feeding and daytime feeding induced by insulin (10 mg/kg) is also assessed in estrogen and Compound A treated rats. Spontaneous nocturnal feeding is significantly suppressed by ethynyl estradiol (0.1 mg/kg), but Compound A treated rats (10 mg/kg) did not exhibit significant suppression. Insulin-induced feed is not significantly affected by either ethynyl estradiol or Compound A. This indicates an inhibition of feeding, yet the type of hyperphagic stimulus is important.

ASSAY 3

Five to fifty women are selected for the clinical study. The women are post-menopausal, i.e., have ceased menstruating for between 6 and 12 months prior to the study's initiation, are in good general health, and are overweight (at least 15% above acceptable weight for the person's height). The study has a placebo control group, i.e., the women are divided into two groups, one of which receives the active agent of this invention and the other receives a placebo. Women in the test group receive between 50–200 mg of the active agent per day by the oral route. They continue this therapy for 3–12 months. Accurate records are kept as to the weights of the patients in both groups and at the end of the study these results are compared. The results are compared both between members of each group and also the results for each patient are compared to the weights reported by each patient before the study began.

Utility of the compounds of the invention is illustrated by the positive impact they have on weight gain/loss or appetite inhibition when used in at least one study above.

We claim:

1. A method of inhibiting weight gain or inducing weight loss comprising administering to a human an effective amount of a compound having the formula

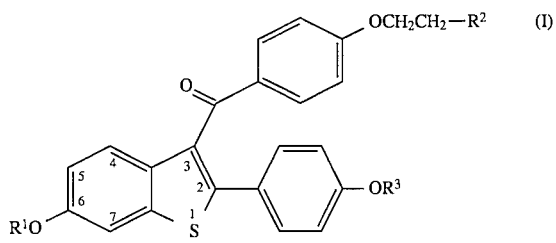

wherein $R^1$ and $R^3$ are independently hydrogen, —$CH_3$,

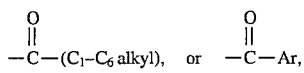

wherein Ar is optionally substituted phenyl;

$R^2$ is piperidino; or a pharmaceutically acceptable salt of solvate thereof.

2. The method of claim 1 wherein said compound is the hydrochloride salt thereof.

3. The method of claim 1 wherein said administration is prophylactic.

4. The method of claim 1 wherein said compound is

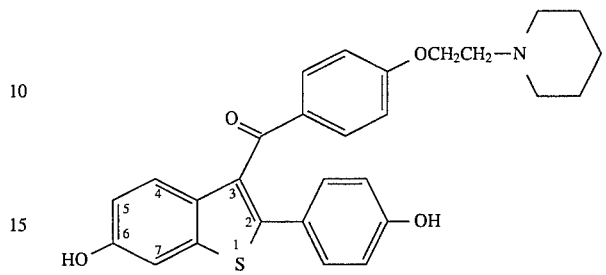

or its hydrochloride salt.

5. The method of claim 1 wherein said human is a post-menopausal woman.

* * * * *